United States Patent
Morton et al.

(10) Patent No.: US 10,857,169 B2
(45) Date of Patent: Dec. 8, 2020

(54) TOBRAMYCIN MAGNESIUM STEARATE MICROPARTICLES FOR INHALATION, COMPOSITIONS THEREOF, AND METHODS OF MAKING AND USING THE SAME

(75) Inventors: David Morton, Parma (IT); Qi Zhou, Parma (IT); Rossella Musa, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 84 days.

(21) Appl. No.: 12/967,306

(22) Filed: Dec. 14, 2010

(65) Prior Publication Data

US 2011/0139152 A1 Jun. 16, 2011

(30) Foreign Application Priority Data

Dec. 14, 2009 (EP) .................................. 09179010

(51) Int. Cl.
| | |
|---|---|
| *A61M 15/00* | (2006.01) |
| *A61K 9/50* | (2006.01) |
| *A61K 31/7036* | (2006.01) |
| *A61P 31/04* | (2006.01) |
| *A61P 11/00* | (2006.01) |
| *A61K 9/00* | (2006.01) |
| *A61K 9/14* | (2006.01) |

(52) U.S. Cl.
CPC ........ *A61K 31/7036* (2013.01); *A61K 9/0075* (2013.01); *A61K 9/145* (2013.01); *A61K 9/5015* (2013.01); *A61K 9/5089* (2013.01)

(58) Field of Classification Search
CPC ........... A61P 31/06; A61P 11/00; A61P 31/04; A61K 9/2015; A61K 9/0075; A61K 31/7036; A61K 9/5089
See application file for complete search history.

(56) References Cited

U.S. PATENT DOCUMENTS

| 5,508,269 A | 4/1996 | Smith et al. |
| 2004/0071635 A1* | 4/2004 | Staniforth et al. ............ 424/46 |
| 2006/0073105 A1 | 4/2006 | Yamashita et al. |
| 2008/0214481 A1* | 9/2008 | Challoner et al. ............. 514/37 |
| 2011/0182960 A1 | 7/2011 | Van Dongen et al. |

FOREIGN PATENT DOCUMENTS

| EP | 1 402 913 | 3/2004 |
| EP | 2 050 437 | 4/2009 |
| WO | 2010/003465 | 1/2010 |

OTHER PUBLICATIONS

Stein et al. "Mechanofusion for High Performance Particles," Process Engineering (DKG), 2002, 79(4), pp. E11-E15.*
Parlati et al. "Pulmonary Spray Dried Powders of Tobramycin Containing Sodium Stearate to Improve Aerosolization Efficiency," May 2009, 26(5), Pharm. Res., pp. 1084-1092.*
European Search Report in Application No. 09179010.5, dated Jun. 8, 2010.
Pilcer et al., "European Journal of Pharmaceutics and Biopharmaceutics", vol. 68, No. 2, (2008), pp. 413-421.
Gabrielle Pilcer et al., "Pharmaceutical Research", vol. 23, No. 5, May 2, 2006, pp. 931-940.
F. Buttini et al., Respiratory Drug Delivery, (2012) pp. 835 to 839.
http://www.medicines.org.uk/emc/medicine/22837 (13pgs) (2013).
J.S. Patton et al., Proc. Am Thorac Soc. vol. 1, pp. 338-344 (2004).
T. S. Cavaiola et al., Clinical Therapeutics, vol. 36, No. 8, pp. 1275-1289 (2014).
Q. Zhou et al., Adv. Drug Deliv. Rev. (2014) (17 pages).
L. L. Ioannides-Demos et al., Antimicrobial Agents and Chemotherapy, vol. 42, No. 6, (1998) p. 1365-1369.
C. G. Prober et al., Pediatrics, vol. 106, No. 6 (2000) pp. 8.
G. F. Cooney et al., J. Clin Pharmacol. (1994), vol. 34 pp. 255-259.

* cited by examiner

*Primary Examiner* — Mina Haghighatian

(74) *Attorney, Agent, or Firm* — Oblon, McClelland, Maier & Neustadt, L.L.P.

(57) ABSTRACT

Powder formulations for inhalation which comprise microparticles containing an antibiotic and magnesium stearate are useful for the treatment of bacterial infections associated with certain pulmonary diseases.

10 Claims, 1 Drawing Sheet

FIG. 1A
FIG. 1B
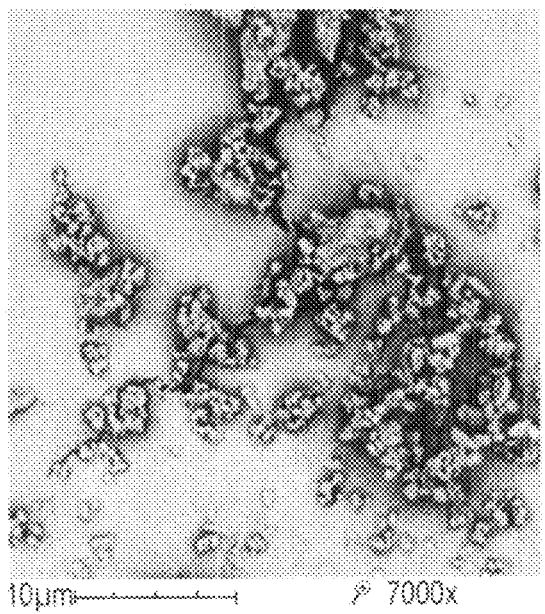
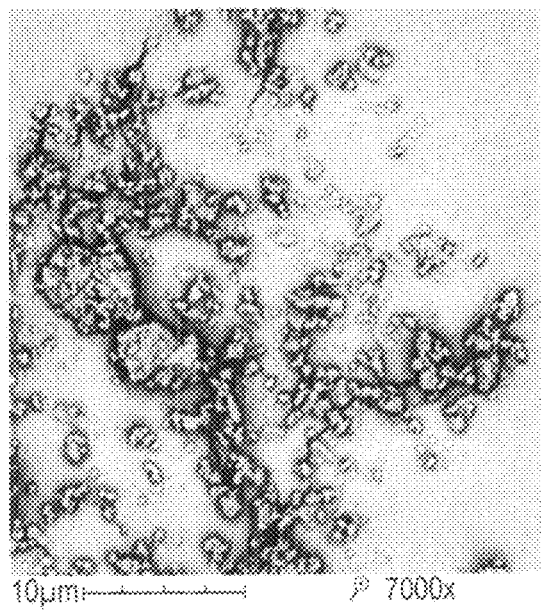

TOBRAMYCIN MAGNESIUM STEARATE MICROPARTICLES FOR INHALATION, COMPOSITIONS THEREOF, AND METHODS OF MAKING AND USING THE SAME

CROSS REFERENCES TO RELATED APPLICATIONS

This application claims priority to European Patent Application No. 09179010.5, filed on Dec. 14, 2009, which is incorporated herein by reference in its entirety.

BACKGROUND OF THE INVENTION

Field of the Invention

The present invention relates to formulations for inhalation comprising microparticles containing an antibiotic and magnesium stearate. The present invention also relates to processes for preparing such microparticles and to their use in the treatment of bacterial endobronchial infections associated with certain pulmonary diseases.

Discussion of the Background

Cystic fibrosis, also known as CF, mucovoidosis or mucoviscidosis, is a fatal genetic disorder. Although technically it is considered a rare disease, cystic fibrosis is ranked as one of the most widespread life-shortening genetic diseases and it affects more than 60,000 people worldwide. It is associated with impairment in the transport of chloride ions across the epithelial membranes of exocrine glands, which causes a decreased water content of their secretions. Morphological changes of dilation and hypertrophy of the bronchial glands are followed by mucous plugging. Said viscid mucus in the airways allows bacterial colonization, with consequent infection of the respiratory tract, contributing to ongoing tissue damage.

*Haemophilus influenzae* and *Staphylococcus aureus* are the first pathogens, which colonize the airway in childhood. As the lung disease progresses, colonization by the pathogen *Pseudomonas aeruginosa* will follow. After a period of intermittent colonization with *Pseudomonas aeruginosa*, the colonization becomes chronic in most CF patients, and virtually impossible to be eradicated.

Among others, antibiotics belonging to the family of aminoglycosides, and in particular tobramycin, are yet currently utilized via parenteral route. Said antibiotics oppose the CF progression by reducing pulmonary deterioration and improving lung function.

However, aminoglycosides penetrate endobronchial secretions (sputum) poorly, necessitating large intravenous doses to attain an efficacious concentration at the site of infection. These high doses place the patient at risk for nephrotoxic and ototoxic effects. These problems could be overcome by administering the drugs to the lungs through aerosolization, as by this route, said antibiotics are poorly absorbed across lung epithelial surfaces, while remaining chemically stable.

In particular aqueous formulations for the administration of tobramycin [(2S,3R,4S,5S,6R)-4-amino-2-{[(1S,2S,3R,4S,6R)-4,6-diamino-3-{[(2R,3R,5S,6R)-3-amino-6-(aminomethyl)-5-hydroxyoxan-2-yl]oxy}-2-hydroxycyclohexyl]oxy}-6-(hydroxymethyl)oxane-3,5-diol] by different types of nebulizers are currently on the market under the trademark of TOBI® (Novartis Pharm Corp) and BRAMITOB® (Chiesi Farmaceutici SpA). However, nebulization does not completely satisfy the patient's compliance as patients need hospital or home setting delivery devices. Moreover, many reports have shown bacterial contamination of nebulizers used by CF patients, making necessary their regular cleaning and disinfecting. Another drawback of nebulisers may be their low efficiency.

Powder formulations to be administered by suitable devices, known as Dry Powder Inhalers (DPIs) may be considered a suitable alternative to tobramycin formulations for nebulisation, as these systems could provide easier and more rapid drug administration. In particular, due to their high therapeutic dose, capsule-based Dry Powder Inhalers should be considered suitable devices.

Some of the problems to be solved in providing an efficacious tobramycin dry powder formulation are those normally faced in manufacturing said kind of formulations, to say it should exhibit suitable flowability, adequate chemical and physical stability in the device before use, and give rise to a good respirable fraction as well as deliver an accurate therapeutically active dose of the active ingredient. In particular, due to the high dose and hence the high powder loading in each capsule (equal to or higher than 15 mg), it is required that formulation exhibits suitable flow properties to allow an efficient emptying of the capsule upon actuation of the inhaler, and hence a reproducible emitted dose.

Moreover, it is well known that tobramycin is hygroscopic. Since, besides affecting chemical stability, humidity could also affect flowability, particular attention should be paid in reducing the amount of residual water as well as the water uptake after storage.

These tasks of making tobramycin formulation for DPI appear not to be easily solved as currently no product has been marketed yet.

WO 03/053411 and WO 2006/066367 discloses tobramycin formulations comprising phospholipids. However, their use introduces concerns regarding their physico-chemical stability.

More recently Parlati et al (*Pharm. Res.*, 2009, 26 (5), 1084-1092) presented data about a powder of tobramycin containing sodium stearate prepared by spray-drying.

However, there is still a need for a powder comprising antibiotics belonging to the family of aminoglycosides, such as tobramycin, suitable for DPI administration. In particular, it would also be highly advantageous to provide a formulation easy to be manufactured without the use of solvents, and in particular without the use of aqueous solvents as residual water could affect chemical stability and/or flowability of the powder. The problems and the drawbacks of the prior art are solved by the formulation of the present invention.

SUMMARY OF THE INVENTION

Accordingly, it is one object of the present invention to provide novel dry powder formulations for pulmonary administration of an antibiotic belonging to the family of aminoglycosides, which alleviate the drawbacks discussed above.

It is another object of the present invention to provide novel processes for preparing such a formulation.

It is another object of the present invention to provide novel methods for the treatment of bacterial endobronchial infections associated with certain pulmonary diseases by administering such a formulation.

These and other objects, which will become apparent during the following detailed description, have been achieved by the inventors' discovery that a dry powder formulation for pulmonary administration comprising mechano-fused microparticles containing particles of an antibiotic belonging to the family of aminoglycosides in an amount equal to or higher than 90% w/w and magnesium stearate in an amount equal to or lower than 10% w/w, wherein magnesium stearate coats the surface of the drug particles by at least 50%, and optionally a physiologically acceptable pharmacologically-inert carrier, are effective for the treatment of bacterial endobronchial infections associated with certain pulmonary diseases.

Preferably the antibiotic is tobramycin.

In another aspect, the present invention provides such mechano-fused microparticles.

The present invention also provides a capsule for use with a dry powder inhaler filled with the dry powder formulation of the invention.

In a further aspect, the present invention provides a method for preparing the microparticles of the invention by mechano-fusion.

In a further aspect, the present invention provides microparticles containing particles of an antibiotic belonging to the family of aminoglycosides in an amount equal to or higher than 90% w/w and magnesium stearate in an amount equal to or lower than 10% w/w, wherein magnesium stearate coats the surface of the drug particles by at least 50%, obtainable by mechano-fusion.

The present invention is also directed to the mechano-fused microparticles of the invention for use for the treatment of an endobronchial bacterial infection associated to a pulmonary disease.

The present invention is further directed to the use of the mechano-fused microparticles of the invention in the manufacture of a medicament for the treatment of an endobronchial bacterial infection associated to a pulmonary disease.

In yet another aspect, the present invention is directed to the mechano-fused microparticles of the invention for the treatment of an endobronchial bacterial infection associated to a pulmonary disease.

In an even further aspect, the present invention provides a method for treating an endobronchial bacterial infection associated to a pulmonary disease in a patient, comprising administering a therapeutically effective amount of the mechano-fused microparticles of the invention.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIGS. 1(a) and (b) show pictures taken by SEM of the mechano-fused microparticles of invention consisting of: (a) 99% tobramycin and 1% magnesium stearate; (b) 95% tobramycin and 5% magnesium stearate.

DETAILED DESCRIPTION OF THE PREFERRED EMBODIMENTS

The terms "active drug," "active ingredient," "active," "active substance," "active compound," and "therapeutic agent" are used as synonymously.

Dry powder inhalers can be divided into two basic types:
i) single dose inhalers, for the administration of single subdivided doses of the active compound; each single dose is usually filled in a capsule;
ii) multidose dry powder inhalers, pre-loaded with quantities of active principles sufficient for longer treatment cycles.

The term "coat" means that the lubricant magnesium stearate forms a film around the active particles. The coating is only partial when the amount of magnesum stearate is not sufficient for forming a film around the whole surface of all the particles of the active ingredient.

The term "substantially pure" means an active ingredient having a chemical purity higher than 90% w/w, preferably equal to or higher than 93% w/w.

In general terms, the particle size of particles is quantified by measuring a characteristic equivalent sphere diameter, known as volume diameter, by laser diffraction. The particle size can also be quantified by measuring the mass diameter by means of suitable instruments well known to the skilled person.

The volume diameter (VD) is related to the mass diameter (MD) by the density of the particles (assuming a size independent density for the particles).

The term "mechano-fused" refers to microparticles constituted of two different materials wherein a first material is mechanically fused onto a second by a dry process.

The particle size is expressed in terms of volume diameter and the particle size distribution is expressed in terms of: i) the volume median diameter (VMD) which corresponds to the diameter of 50 percent by weight or volume respectively, of the particles, and ii) the volume diameter (VD) in micron of 10% and 90% of the particles, respectively.

The term "agglomerated" is used herein with two different meanings. The term "stable agglomerated microparticles" refers to particles which consist of more than one microparticles, those microparticles being adhered to each other. For example, an agglomerated microparticle of [d(v,0.5)] of 1.5 micron may consist of a large number of microparticles each having a lower diameter, adhered together.

On the contrary, the term "loose-agglomerated microparticles" refers to particles in form of soft agglomerates which could easily break-up to give rise to the single microparticles.

The term "suitable flow properties" refers to a formulation that is easy handled during the manufacturing process and is able of ensuring an accurate and reproducible delivering of the therapeutically effective dose. The expression "accurate therapeutically active dose of the active ingredient" refers to a formulation wherein, upon actuation, the mean emitted dose is equal to or higher than 60% of the nominal dose, preferably higher than 65%, even more preferably higher than 70%.

The expression "chemically stable" refers to a formulation that, upon storage, meets the requirements of the EMEA Guideline CPMP/QWP/122/02 referring to "Stability Testing of Existing Active Substances and Related Finished Products".

The expression "physically stable" refers to a formulation that does not change its physical state in the device before use and upon storage.

The expression "respirable fraction" refers to an index of the percentage of active particles which would reach the deep lungs in a patient.

The respirable fraction, also termed fine particle fraction (FPF), is evaluated using a suitable in vitro apparatus, typically the Multistage Cascade Impactor or Multi Stage Liquid Impinger (MLSI) according to procedures reported in common Pharmacopoeias. However other apparatus such as Twin Stage Apparatus or SprayTec instrument, as reported in the Examples, may be advantageously used. It is calculated by the ratio between the respirable dose, corresponding to particles having a diameter smaller than about 5 micron and the delivered (emitted) dose.

A respirable fraction (FPF) significantly higher than 30% is an index of good aerosol performances.

The term "therapeutically effective amount" means the amount of the antibiotic belonging to the family of aminoglycosides, that, when delivered to the lungs via a dry powder formulation as described herein, provides the desired biological effect.

The invention is based in part on the finding that dry coating the active particles of an antibiotic belonging to the family of aminoglycosides such as tobramycin with magnesium stearate by mechano-fusion increases the aerosol performances of said particles.

Therefore, in a first aspect, the invention relates to a dry powder formulation for pulmonary administration comprising mechano-fused microparticles containing particles of an antibiotic belonging to the family of aminoglycosides in an amount equal to or higher than 90% w/w and magnesium stearate in an amount equal to or lower than 10% w/w.

In one embodiment, the mechano-fused microparticles comprise particles of an antibiotic belonging to the family of aminoglycosides in an amount equal to or higher than 90% w/w and magnesium stearate in an amount equal to or lower than 10% w/w. In another embodiment, the mechano-fused microparticles consist essentially of particles of an antibiotic belonging to the family of aminoglycosides in amount equal to or higher than 90% w/w and magnesium stearate in an amount equal to or lower than 10% w/w. In yet another embodiment, the mechano-fused microparticles consist of particles of an antibiotic belonging to the family of aminoglycosides in an amount equal to or higher than 90% w/w and magnesium stearate in an amount equal to or lower than 10% w/w.

The antibiotic belonging to the family of aminoglycosides can be advantageously selected from the group consisting of tobramycin, kanamycin A, dibekacin, amikacin and arbekacin.

Said aminoglycosides in the microparticles of the invention may be used as a base or as a pharmaceutically acceptable salt thereof such as sulfate, nitrate, chloride, and bromide.

The preferred antibiotic is tobramycin which is preferably used as a base. When used as a salt, the preferred one is tobramycin sulfate in the 2:5 stoichiometric ratio. Alternatively, other tobramycin salts may be used, such as the nitrate salt.

Magnesium stearate in the microparticles of the invention is present in an amount equal to or lower than 10% w/w. Advantageously, magnesium stearate is present in an amount of 0.1 to 10%, more advantageously 0.5 to 5% w/w.

In one embodiment, the amount may also be 0.5 to 2% w/w. In other embodiments instead, the amount may be 5 to 10% w/w or 2 to 5% w/w.

In a particular preferred embodiment, the amount is 0.5 to 1.0% w/w.

The remaining part of the antibiotic can be calculated accordingly.

For the microparticles of the invention, it is required that magnesium stearate coats at least 50% of the surface of the drug particles, advantageously at least 60%, preferably at least 75%, more preferably at least 80%. Of course, the upper limit of the percent of the surface which may be coated is 100%.

The presence of a coating can be qualitatively detected by visual methods such as Scanning electron microscopy (SEM).

The extent of coating instead can be determined according to other known methods. For example, the extent of coating of the microparticles of the invention can be determined by X-ray photoelectron spectroscopy (XPS), a well known tool for determining the extent as well as the uniformity of distribution of certain elements on the surface of other substances. In the XPS instrument, photons of a specific energy are used to excite the electronic states of atoms below the surface of the sample. Electrons ejected from the surface are energy filtered via a hemispherical analyser (HSA) before the intensity for a defined energy is recorded by a detector. Since core level electrons in solid-state atoms are quantized, the resulting energy spectra exhibit resonance peaks characteristic of the electronic structure for atoms at the sample surface.

Typically XPS measurements are taken on an Axis-Ultra instrument available from Kratos Analytical (Manchester, UK) using monochromated Al Kα radiation (1486.6 eV) operated at 15 mA emission current and 10 kV anode potential (150 W). A low energy electron flood gun is used to compensate for insulator charging. Survey scans, from which quantification of the detected elements are obtained, are acquired with analyser pass energy of 160 eV and a 1 eV step size. High-resolution scans of the C 1s, O 1s, Mg 2s, N 1s and Cl 2p regions are acquired with a pass energy of 40 eV and a 0.1 eV step size. The area examined is approximately 700 μm×300 μm for the survey scans and a 110 μm diameter spot for the high-resolution scans.

Typically, an accuracy of 10% is quoted for routinely performed XPS experiments.

Alternatively, the extent to which magnesium stearate coats the surface of the antibiotic can be determined by first measuring the water contact angle of the microparticles, and then applying the equation known in the literature as Cassie and Baxter, reported on page 338 of Colombo I et al *Il Farmaco* 1984, 39 (10), 328-341. The measure of the water contact angle can be carried out as referenced on page 332 of Colombo et al, i.e. by applying the sessile or static drop method that envisions the depositing of a liquid drop onto the surface of the powder in form of disc obtained by compaction (compressed powder disc method). A wettability tester available from Lorentzen Wettre (Sweden) can be used.

Other tools which may advantageously be used for measuring the extent to which magnesium stearate coats the surface of the antibiotic are IR and Raman spectroscopies coupled to SEM or Time-of-Flight Secondary Ion Mass Spectrometry (TOF-SIMS). Said tools are known to the skilled person in the art and the operative procedures for using them are within his general knowledge.

In contrast to microparticles obtained from solutions such as spray dried microparticles that will have a spherical shape, from FIG. 1, it can also be appreciated that the shape of the mechano-fused microparticles of the invention is irregular and not spherical.

Scanning electron microscopy (SEM) or optical microscopy may be used to qualitatively appreciate the characteristics of the microparticles of the invention such as particles shape and their surface morphology.

The resulting smoothed and lubricated surfaces appear to reduce inter-particulate forces (intermolecular surface forces and frictional forces) within the powder, thus giving rise to better dispersion performance during the aerosolization.

The mechano-fused microparticles of the present invention may be crystalline or amorphous. However, the percentage of amorphicity, expressed as weight % with respect to the total weight of the microparticles, may greatly vary and it may be equal to or higher than 50%, preferably of at least 70%, even more preferably of at least 90%. Said percentage of amorphicity may be determined using X-ray powder diffraction or other known techniques known to the skilled person such as differential scanning calorimetry (DSC) or microcalorimetry.

The particle size of the microparticles of the present invention is lower than 15 microns. Advantageously, at least 90% of the particles have a volume diameter lower than about 10 microns. More advantageously, no more than 10% of the microparticles have a volume diameter [d(v,0.1)] lower than 0.1 micron. Preferably no more than 50% of particles have a volume diameter [d(v,0.5)] lower than 0.6, and preferably the [d(v,0.5)] is 0.7 to 2.0 microns, more preferably 0.8 to 1.5 microns.

The particle size method could be measured by laser diffraction according to known methods.

The mechano-fused microparticles of the present invention may be present in the form of unagglomerated, e.g., individual, or stable agglomerated microparticles, those stable agglomerated microparticles having a particle size comprised in one of the ranges described above.

The microparticles of the present invention exhibit a very low amount of residual water, e.g. lower than 5.0% w/w, preferably 4.8% to 4.5% w/w, as determined according to known methods such as Karl-Fisher method.

It has indeed been found that the amount of residual water in the microparticles of the present invention does not significantly increase in comparison to the antibiotic as such. It has also been found that magnesium stearate, while coating, at least partially, the surface of the active ingredient particles, is able of protecting the microparticles from the humidity of the environment.

As reported above, since, besides affecting chemical stability, humidity could also be detrimental to the flowability, this could be considered a further advantage. As for the flowability, the microparticles of the present invention also exhibits the following characteristics:
 a poured density of 0.16 to 0.35 g/ml;
 a tapped density of 0.25 to 0.60 g/ml;
 a Can index lower than 50%, preferably equal to or lower than 46%, more preferably lower than 40%.

Said technological characteristics make the relevant formulations suitable for pulmonary administration by a capsule-based Dry Powder Inhaler.

Said formulation may consist of only the microparticles of the invention or may comprise a physiologically acceptable pharmacologically-inert carrier. Such carrier may serve simply as bulking agent when it is desired to reduce the active agent concentration in the powder which is being delivered to a patient or may serve to improve the dispersability of the powder within a powder dispersion device in order to provide more efficient and reproducible delivery of the active agent and to improve the handling characteristics of the active agent (e.g., flowability and consistency) to facilitate manufacturing and powder filling.

The carrier may be any amorphous or crystalline physiologically acceptable inert material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate.

The formulation may also comprise one or more active ingredients, preferably another antibiotic for the treatment by inhalation of a bacterial infection or other suitable excipients such as flavoring and taste masking agents.

The formulations of the present invention containing the microparticles of the present invention give rise, upon aerosolization, to an excellent respirable fraction, advantageously higher than 30%, more advantageously higher than 35%, preferably higher than 40%, more preferably higher than 50%.

The emitted dose may be advantageously higher than 60%, preferably higher than 70%.

In some particular embodiments, when the amount of magnesium stearate is comprised between 0.5 and 1.0%, to further improve both the emitted dose and the respirable fraction, the microparticles of the present invention may be subjected to loose agglomeration to obtain loose-agglomerated microparticles, preferably by vibrating the powder between two sieves of 180 and 710 μm.

In a further aspect, the present invention provides a method for preparing the microparticles of the present invention by mechano-fusion.

Mechano-fusion is a simple, dry mechanical process that is designed to apply thin layers of lubricants to the particle surfaces.

The fine active particles and the magnesium stearate particles are fed into the mechano-Fusion driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall). The particles violently collide against each other with enough energy to locally heat and soften, break, distort, flatten and wrap the particles of hydrophobic material around the core particle to form a coating. The energy is generally sufficient to break up agglomerates, while the particle size of the active ingredient remains substantially the same.

Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball mills. Also, preferably, no impaction of milling media surfaces is present so that wear and consequently contamination are minimized.

A scraper may also be present to break up any caked material building up on the vessel surface. This is particularly advantageous when using fine cohesive starting materials. The local temperature may be controlled by use of a heating/cooling jacked built into the drum vessel walls. The powder may be re-circulated through the vessel.

Apparatus such as Nobilta® and Nanocular® mechanofusion processors from Hosokawa Micron Corporation, Japan, are preferably utilized. Both systems comprise a cylindrical vessel with a rotating axial shaft. In the Nobilta® processor, the paddles extend along the length of the axial shaft, and extend out to within approximately 1 mm of the vessel wall. Consequently, as the shaft rotates, the blades continuously sweep close to the vessel wall, ensuring all the powder is in constant and violent motion. Due to the high rotational speed of the paddles, the powder is propelled towards the wall, and as a result the mixture experiences very high shear forces at the paddle face, and compressive stresses between wall and paddle.

In the Nanocular® processor, the motion is similar, but with less impact due to absence of the paddle faces, and a higher degree of compressive stresses between wall and press head.

The time of the process will depend on the specific processor, and it may be suitably adjusted by the skilled person depending on the size of the batch. In some embodiments the process may be carried out for a time of at least 2 minutes, preferably for at least 5 minutes, more preferably for at least ten minutes. In some embodiments of the invention, the time of process may be 10 to 20 minutes. Also, the speed of rotation shall depend on the specific mechanofusion processor and size of batch processed. Typically, a speed of rotation not higher than 10000 rpm may be utilized, advantageously not higher than 6000 rpm, preferably 1000 to 5000 rpm, more preferably 2000 to 3000 rpm.

Alternatively, the speed of rotation may be defined as speed as tip speed in m/s rather than in rpm. The tip speed will depend on the rotor diameter. Given a rotor diameter of approximately 9.2 cm, the tip speed which may advantageously be used is higher than 5 m/s, preferably higher than 10 m/s, more preferably higher than 25 m/s.

Other similar apparatus such as Cyclomix® (Hosokawa) and Hybridiser (Nara) may be advantageously utilized.

Upon preparation of the microparticles by the above described method, the antibiotic in the microparticles remains substantially chemically pure.

The dosage of the antibiotic in the microparticles of the invention can vary within wide limits depending on the nature of bacterial infection, type of disease to be treated and the type of patient.

A person skilled in the art can determine a therapeutically effective amount for each patient and thereby define the appropriate dosage. When tobramycin is used, a typical single unit dose for treating by inhalation *Pseudomonas aeruginosa* endobronchial infection associated to cystic fibrosis might fall within the range of 20 mg to 160 mg (calculated as free base), preferably 30 to 90 mg, to be administered to the patient from once daily to three times a day.

Depending on the DPI device, the single unit dose may be administered from a single container, or, preferably, it may be divided into multiple containers, such as capsules for sequential administration, or from more than one container, disposed within the DPI device. Therefore, separately, each capsule is filled with less than a single unit dose.

For example, the single unit dose may be divided into two to six capsules, preferably form three to five capsules.

When tobramycin is used, typically, each capsule is filled with 12 to 40 mg expressed as free base, preferably 15 to 30 mg.

In one of the preferred embodiments, to improve the respirable fraction, the powder load of each capsule is 15 mg.

Any capsule for pharmaceutical use may be utilized, for example size 3 HPMC or gelatine capsules.

The formulation of the present invention may be of use in the treatment of any endobronchial bacterial infection associated to a pulmonary disease such as cystic fibrosis (CF), non-CF bronchiectasis, pneumonia, chronic pulmonary obstructive disease, and tuberculosis. Preferably it may be of use in the treatment of infection from Gram-negative bacteria such as *Pseudomonas aeruginosa*.

In particular, the formulation of the present invention may be utilized for the treatment of patients with cystic fibrosis who are known to be colonized with *Pseudomonas aeruginosa*.

In summary, the advantages of the microparticles of the present invention include the fact that the relevant formulation is physically and chemically stable, less susceptible to water uptake, gives rise to a high respirable fraction, ensures an accurate and reproducible delivery of the therapeutically effective dose, and is more easily and economically manufactured than known formulations.

Other features of the invention will become apparent in the course of the following descriptions of exemplary embodiments which are given for illustration of the invention and are not intended to be limiting thereof.

EXAMPLES

Example 1. Preparation of Microparticles According to the Invention

Micronized tobramycin and various amounts of magnesium stearate at 0.5%, 1%, 5%, and 10% w/w are fed into the Nobilta® on Nanocular® driven vessel. The process was conducted at a batch size of approximately 40 ml for 10 and 20 minutes processing time at process rotation speed of 5000 rpm. The obtained mechano-fused microparticles were collected and subjected to technological and aerosol performances characterization. Similarly, microparticles with other antibiotics belonging to the class of aminoglycosides can be obtained.

Example 2. Technological Characterization of the Microparticles of Example 1

The microparticles as obtained in Example 1 were subjected to the following analysis.

Scanning electron microscopy (SEM). Morphological properties were investigated using a scanning electron microscope (Phenom™, FEI Company, Hillsboro, Oreg.). Each sample was carefully mounted on a sample holder, so as to ensure representative images, and sputter coated with gold. SEM micrographs were taken using in-built image capture software. Representative pictures are reported in FIGS. (a) and 1(b). The particle size and the shape of the microparticles of the invention do not substantially change in comparison to tobramycin as such but a lesser number of loose agglomerates are present in the powder.

Densities and flow characteristics. Both density values were calculated by the method reported in the European Pharmacopeia. The poured density (dv) was measured by pouring samples slowly into a 10 ml calibrated measuring cylinder through a funnel at a fixed height above the cylinder. The tapped density (ds) was determined after 1250 taps using an automatic tapper (AUTOTAP™, Quantachrome Instruments, Boynton Beach, Fla., USA). The tapper operated with a 3.18 mm vertical travel at a tapping speed of 260 tap/minute. The Can index (CI) was calculated from poured density and tapped density using the following equation:

$$CI(\%) = \frac{ds - dv}{ds} \times 100$$

Particle size via laser diffraction. Particle size distributions were measured by laser diffraction (Mastersizer® S, Malvern Instruments, Worcestershire, UK) using the 300 RF lens equipped with a small volume sample presentation unit (capacity 150 ml). The powders were dispersed in 0.065% of Dioctyl Sulfosuccinate Sodium salt in n-hexane. The sample was sonicated in the dispersant for 5 minutes prior to measurement.

The results in terms of density, Can Index and particle size (mean+relative standard deviation) are reported in Table 1, in which TMC stands for tobramycin and MgSt stands for magnesium stearate.

TABLE 1

Densities, Carr Index and particle size.

| Batch | | poured density (g/ml) | tapped density (g/ml) | Carr index | D10 (μm) | D50 (μm) | D90 (μm) |
|---|---|---|---|---|---|---|---|
| TMC 10% MgSt mechanofused nobilta 10 min | Mean | 0.30 | 0.53 | 0.43 | 0.13 | 0.89 | 9.47 |
| | RSD | 0.02 | 0.02 | 0.03 | 0.04 | 0.08 | 0.02 |
| TMC 10% MgSt mechanofused nobilta 20 min | Mean | 0.31 | 0.58 | 0.46 | 0.14 | 0.90 | 9.32 |
| | RSD | 0.01 | 0.02 | 0.02 | 0.04 | 0.11 | 0.03 |
| TMC 5% MgSt mechanofused nobilta 10 min | Mean | 0.28 | 0.51 | 0.46 | 0.14 | 0.96 | 9.03 |
| | RSD | 0.01 | 0.01 | 0.01 | 0.04 | 0.09 | 0.03 |
| TMC 5% MgSt mechanofused nobilta 20 min | Mean | 0.28 | 0.52 | 0.46 | 0.14 | 0.80 | 8.65 |
| | RSD | 0.01 | 0.01 | 0.02 | 0.07 | 0.06 | 0.03 |
| TMC 1% MgSt mechanofused nobilta 10 min | Mean | 0.17 | 0.31 | 0.45 | 0.15 | 1.53 | 7.81 |
| | RSD | 0.01 | 0.03 | 0.03 | 0.08 | 0.11 | 0.02 |
| TMC 1% MgSt mechanofused nobilta 20 min | Mean | 0.18 | 0.33 | 0.45 | 0.19 | 1.23 | 8.30 |
| | RSD | 0.01 | 0.03 | 0.03 | 0.07 | 0.07 | 0.04 |
| TMC 10% MgSt mechanofused nanocular 10 min | Mean | 0.18 | 0.29 | 0.39 | 0.14 | 1.76 | 7.69 |
| | RSD | 0.02 | 0.03 | 0.03 | 0.04 | 0.10 | 0.63 |
| TMC 5% MgSt mechanofused nanocular 10 min | Mean | 0.19 | 0.34 | 0.45 | 0.17 | 1.40 | 10.06 |
| | RSD | 0.02 | 0.04 | 0.05 | 0.08 | 0.15 | 0.05 |
| TMC 1% MgSt mechanofused nanocular 10 min | Mean | 0.16 | 0.27 | 0.43 | 0.13 | 1.54 | 7.85 |
| | RSD | 0.01 | 0.01 | 0.02 | 0.06 | 0.08 | 0.02 |

Table 1 shows that both the poured and tapped densities increased at increasing the content of MgSt, indicating that the tobramycin has been more fully surface coated with MgSt at the higher contents. In general, such changes in density after coating indicate that the cohesion between the microparticles in the powder has been substantially reduced.

Example 3. Aerosol Performances Characterization of the Microparticles of Example 1

The aerosol performance of the microparticles of the present invention were evaluated by laser diffraction (Spraytec, Malvern Instruments, Worcestershire, UK) equipped with an inhalation cell attachment. Approximate 30 mg (or 15 mg in later tests) of each powder was loaded into size 3 HPMC capsules (Capsugel, Peapack, N.J., USA). Before the aerosolization, a stainless steel pin punched each end of the capsule allowing powders to be released from the capsule by providing two holes with diameter about 1 mm. Each capsule was aerosolized using a Monodose inhaler device (Miat S.p.A., Milan, Italy) at flow rate of 60 and 90 L/min. All measurements were made on four replicates at room temperature (20° C., 50% RH). Each measurement was performed over 4 s.

The device retention was calculated as a percentage of powder left both in the capsules and in the inhalers to the total load. The fine particle fraction (FPF) was defined as the amount of drug particle smaller than 5.4 μm as a percentage of the powder emitted from inhaler device.

It should be noted that all powders were tested after removing large agglomerates by gently passing the powders through a 250 μm sieve. The results in terms of mean+RSD are listed in Table 2 (90 L/Min air flow).

TABLE 2

Aerosol performances at 90 L/minute.

| Batch | | Emitted dose (%) | <5.4 μm (%) |
|---|---|---|---|
| TMC-raw | Mean | 70.77 | 32.58 |
| | RSD | 0.02 | 0.13 |
| TMC 10% MgSt mechanofused nobilta 10 min | Mean | 81.86 | 53.26 |
| | RSD | 0.07 | 0.09 |
| TMC 10% MgSt mechanofused nobilta 20 min | Mean | 64.72 | 49.57 |
| | RSD | 0.01 | 0.05 |
| TMC 5% MgSt mechanofused nobilta 10 min | Mean | 67.13 | 63.19 |
| | RSD | 0.04 | 0.05 |
| TMC 5% MgSt mechanofused nobilta 20 min | Mean | 64.70 | 50.13 |
| | RSD | 0.06 | 0.03 |
| TMC 1% MgSt mechanofused nobilta 10 min | Mean | 81.52 | 65.90 |
| | RSD | 0.04 | 0.02 |
| TMC 10% MgSt mechanofused nanocular 20 min | Mean | 79.72 | 41.22 |
| | RSD | 0.05 | 0.13 |
| TMC 5% MgSt mechanofused nanocular 10 min | Mean | 72.33 | 39.96 |
| | RSD | 0.07 | 0.06 |
| TMC 1% MgSt mechanofused nanocular 10 min | Mean | 62.99 | 42.11 |
| | RSD | 0.05 | 0.01 |

The results demonstrate that the untreated drug powder had a relatively poor aerosol performance with a FPF (%<5.4 μm) around 30%.

After mechanofusion, all the batches of the microparticles of the present invention achieved better performances than the untreated drug powder. Somewhat surprisingly, it was found that the mechano-fused batches with the lower MgSt content of 1% could achieve significantly improved dispersion behaviors, in some cases better than the high content MgSt batches.

Example 4. Effect of Loose Agglomeration on the Aerosol Performances

To further improve both the emitted dose and FPF of the mechano-fused microparticles with lower contents of MgSt, e.g. between 0.5% and 1%, loose agglomeration was applied by vibrating powders between two sieves of 180 and 710 μm.

Prior to this sieving process, powders were tumbled to encourage formation of loose agglomerates. The results (mean+RSD) for loosely agglomerated powders are listed in Table 3.

TABLE 3

The aerosol performances at 90 L/min for loosely agglomerated drug powders.

| Batch | 90 L/min | Emitted dose (%) | <5.4 μm (%) |
|---|---|---|---|
| TMC-raw | Mean | 70.77 | 32.58 |
| | RSD | 0.02 | 0.13 |
| TMC 1% MgSt 10 min (unsieved) | Mean | 75.09 | 69.19 |
| | RSD | 0.02 | 0.03 |
| TMC 1% MgSt 10 min (sieved 180-720 um) | Mean | 65.65 | 68.15 |
| | RSD | 0.06 | 0.10 |

TABLE 3-continued

The aerosol performances at 90 L/min for loosely agglomerated drug powders.

| Batch | 90 L/min | Emitted dose (%) | <5.4 μm (%) |
|---|---|---|---|
| TMC 0.5% MgSt 10 min (unsieved) | Mean | 59.35 | 54.43 |
|  | RSD | 0.06 | 0.02 |
| TMC 0.5% MgSt 10 min (sieved 180-710 um) | Mean | 81.17 | 66.90 |
|  | RSD | 0.04 | 0.03 |

The results show that after this loose agglomeration, the emitted dose for the mechano-fused microparticles with low content of MgSt could be slightly improved and the FPF achieved a much improved level.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A capsule for use with a dry powder inhaler, which contains a dry powder formulation for delivery of tobramycin to the lungs, said formulation consisting of mechano-fused microparticles,
    wherein said mechano-fused microparticles consist of:
    (a) particles of tobramycin in an amount of 99 to 99.5% w/w; and
    (b) magnesium stearate in an amount of 0.5 to 1% w/w,
    wherein magnesium stearate coats at least 50% of the surface of the particles of tobramycin,
    wherein said microparticles have an amount of residual water lower than 0.5% w/w,
    wherein said capsule contains 12 to 40 mg of said tobramycin expressed as free base, and
    wherein administration of said formulation from said capsule to the lungs of a subject results in rapid delivery of said tobramycin and local absorption of said tobramycin by said lungs of said subject.

2. A method for preparing a capsule according to claim 1, comprising:
    i) feeding particles of tobramycin and magnesium stearate particles into a driven vessel of a Mechano-Fusion apparatus;
    ii) processing said particles of tobramycin and magnesium stearate particles for a time of at least 2 minutes, to obtain microparticles;
    iii) collecting said microparticles; and
    iv) filling said microparticles into a capsule.

3. A method according to claim 2, wherein said processing is conducted for at least 5 minutes.

4. A method for the treatment of a *Pseudomonas aeruginosa* infection associated with cystic fibrosis, comprising administering an effective amount of tobramycin from a capsule according to claim 1 to a subject in need thereof,
    wherein administration of said formulation from said capsule to the lungs of a subject results in rapid delivery of said tobramycin and local absorption of said tobramycin by said lungs of said subject.

5. A capsule according to claim 1, which contains 15 to 30 mg of said tobramycin expressed as free base.

6. A capsule according to claim 1, which contains 15 mg of said tobramycin expressed as free base.

7. A capsule according to claim 1, wherein said capsule is a 3 HPMC capsule or a gelatine capsule.

8. A capsule according to claim 1, wherein said capsule is a 3 HPMC capsule.

9. A capsule according to claim 1, wherein said capsule is a gelatine capsule.

10. A capsule according to claim 1, wherein said mechano-fused microparticles consist of:
    (a) particles of tobramycin in an amount of 99.5% w/w; and
    (b) magnesium stearate in an amount of 0.5% w/w.

* * * * *